(12) United States Patent
Di Trapani

(10) Patent No.: US 10,408,446 B2
(45) Date of Patent: Sep. 10, 2019

(54) ILLUMINATION DEVICE SIMULATING THE NATURAL ILLUMINATION AND INCLUDING AN INFRARED LIGHT SOURCE

(71) Applicant: COELUX S.r.l., Lomazzo (IT)

(72) Inventor: Paolo Di Trapani, Lomazzo (IT)

(73) Assignee: COELUX S.r.l, Lomazzo (IT)

( * ) Notice: Subject to any disclaimer, the term of this patent is extended or adjusted under 35 U.S.C. 154(b) by 96 days.

(21) Appl. No.: 15/311,145

(22) PCT Filed: May 14, 2015

(86) PCT No.: PCT/IB2015/053567
§ 371 (c)(1),
(2) Date: Nov. 14, 2016

(87) PCT Pub. No.: WO2015/173770
PCT Pub. Date: Nov. 19, 2015

(65) Prior Publication Data
US 2017/0153021 A1    Jun. 1, 2017

(30) Foreign Application Priority Data

May 14, 2014    (IT) .............................. TO2014A0386

(51) Int. Cl.
*F21V 33/00*    (2006.01)
*F21V 3/00*    (2015.01)
(Continued)

(52) U.S. Cl.
CPC ........ *F21V 33/0092* (2013.01); *A61N 5/0618* (2013.01); *F21V 3/00* (2013.01);
(Continued)

(58) Field of Classification Search
CPC ...... F21V 33/0092; F21V 3/00; F21V 7/0008; F21V 13/02; F21V 33/0088; F21S 8/026;
(Continued)

(56) References Cited

U.S. PATENT DOCUMENTS 1,526,523 A    2/1925    Brown et al.
2,614,202 A    10/1952    Jordan
(Continued)

FOREIGN PATENT DOCUMENTS

DE    29715926 U1    12/1997
DE    20310145    11/2003
(Continued)

OTHER PUBLICATIONS

International Search Report from application No. PCT/IB2015/053567 dated Feb. 1, 2016.
(Continued)

*Primary Examiner* — Laura K Tso
(74) *Attorney, Agent, or Firm* — DiBerardino McGovern IP Group LLC

(57) ABSTRACT

Illumination device for illuminating an environment (7), including a visible source (2), which emits a visible beam, and a diffuse light generator (2, 4; 68; 150), which includes an optical structure (4; 64; 150) delimited by an inlet surface (Si; S3), which receives the visible beam, and by an outlet surface (S2). The generator emits from the outlet surface diffuse visible light and direct visible light. The illumination device further includes an infrared optical source (15), which is different from the first visible source and emits an infrared beam so as to impinge on the inlet surface; the optical structure transmits at least one portion of the infrared beam. The illumination system further includes a ventilation system (40) which can be coupled to the environment, which introduces air masses into the environment, in pulsed mode.

26 Claims, 8 Drawing Sheets

(51) Int. Cl.
    *F24F 11/00*         (2018.01)
    *F24F 13/078*       (2006.01)
    *A61N 5/06*         (2006.01)
    *F21V 7/00*          (2006.01)
    *F21V 13/02*        (2006.01)
    *F21S 8/02*          (2006.01)
    *F21Y 113/10*       (2016.01)

(52) U.S. Cl.
    CPC ............ *F21V 7/0008* (2013.01); *F21V 13/02* (2013.01); *F21V 33/0088* (2013.01); *F24F 11/0001* (2013.01); *F24F 13/078* (2013.01); *A61N 2005/0659* (2013.01); *A61N 2005/0662* (2013.01); *F21S 8/026* (2013.01); *F21Y 2113/10* (2016.08)

(58) Field of Classification Search
    CPC .......... A61N 5/0618; A61N 2005/0659; A61N 2005/0662
    USPC .......................... 362/1, 2, 92, 228, 234, 253
    See application file for complete search history.

(56) References Cited

U.S. PATENT DOCUMENTS

| | | | |
|---|---|---|---|
| 8,622,560 B2* | 1/2014 | Di Trapani | G02B 6/001 362/2 |
| 2007/0051883 A1 | 3/2007 | Rains | |
| 2007/0139923 A1 | 6/2007 | Negley et al. | |
| 2011/0216542 A1* | 9/2011 | Di Trapani | G02B 6/001 362/311.01 |
| 2011/0230131 A1 | 9/2011 | Gao | |
| 2012/0025838 A1* | 2/2012 | Lee | F21S 8/006 324/501 |
| 2012/0149291 A1 | 11/2012 | Roderick et al. | |
| 2013/0261809 A1 | 10/2013 | Morrow | |
| 2014/0133125 A1* | 5/2014 | Di Trapani | F21V 3/0625 362/2 |
| 2017/0051893 A1* | 2/2017 | Di Trapani | F21S 8/04 |

FOREIGN PATENT DOCUMENTS

| | | | |
|---|---|---|---|
| DE | 10256383 | | 6/2004 |
| EP | 0930466 | | 7/1999 |
| EP | 2106198 | A1 | 9/2009 |
| EP | 2549179 | | 1/2013 |
| EP | 3 075 368 | * | 10/2016 |
| GB | 2 408 321 | * | 5/2005 |

OTHER PUBLICATIONS

Denis Cosnard, Italian Search Report, counterpart Italian Application No. TO2014A000386, dated Jan. 26, 2015, 8 pages total.

* cited by examiner

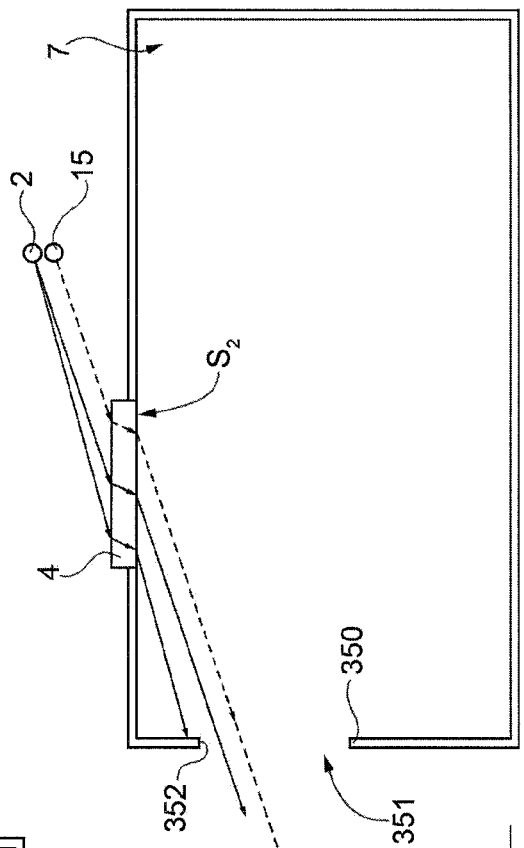
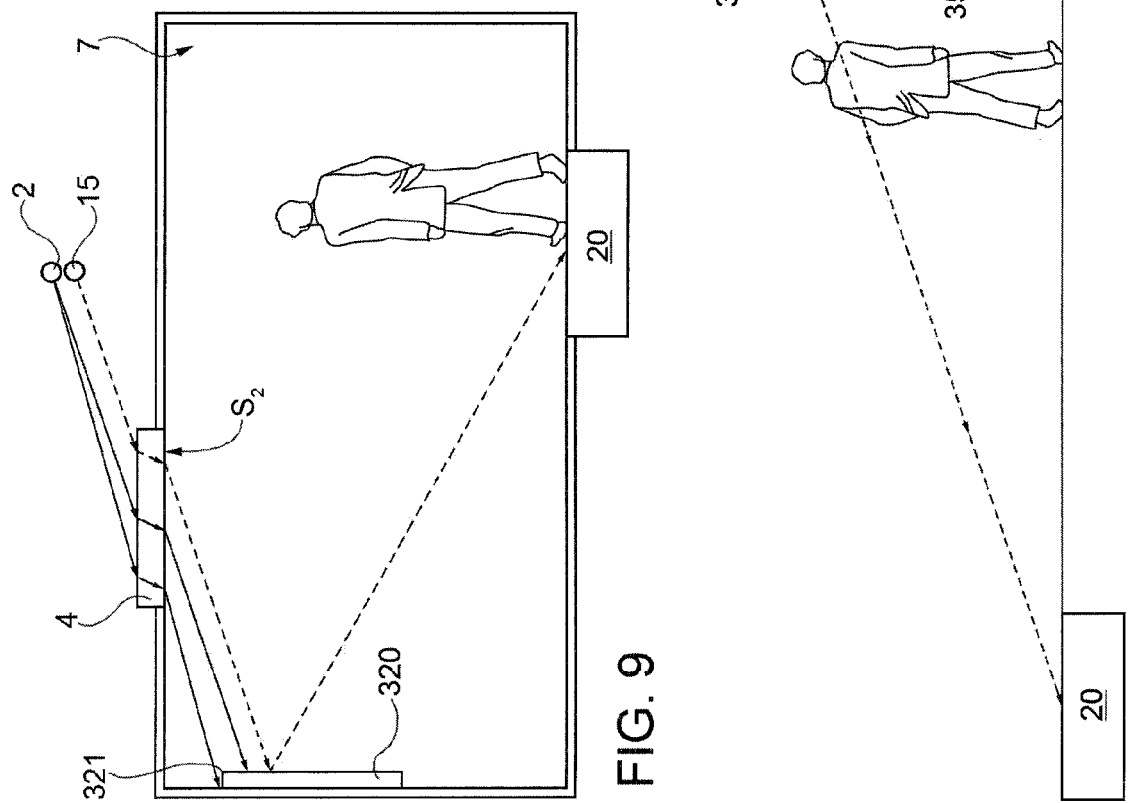

ILLUMINATION DEVICE SIMULATING THE NATURAL ILLUMINATION AND INCLUDING AN INFRARED LIGHT SOURCE

CROSS REFERENCE TO RELATED APPLICATIONS

This application is a U.S. Nationalization of PCT Application Number PCT/IB2015/053567, filed on May 14, 2015, which claims priority to Italian Patent Application No. TO2014A000386, filed on May 14, 2014, the entireties of which are incorporated herein by reference.

TECHNICAL FIELD

The present invention concerns an illumination device which simulates natural illumination and includes an infrared light source.

BACKGROUND ART

It is known that artificial illumination devices are currently available for indoor environments, designed to improve the visual comfort of the users. In particular, illumination devices are known which simulate natural illumination, i.e. the type of illumination present in outdoor environments. The well-known characteristics of natural illumination depend on the interaction between the light rays produced by the sun and the earth's atmosphere.

For example, the European patent application EP2304480 describes an illumination device which comprises a light source, apt to generate visible light, and a panel containing nanoparticles. In use, the panel receives the light rays coming from the light source and acts as a so-called Rayleigh diffuser, i.e. it scatters the light rays analogously to what occurs in the earth's atmosphere in clear sky conditions. Further details relative to the panel as per the European patent application EP2304480 are described in the European patent application EP2304478.

In particular, the illumination device described in the European patent application EP2304480 simulates natural illumination as it generates, within an environment illuminated by it, direct light having low correlated colour temperature (CCT), which simulates the direct light coming from the sun and generates shadows, in the presence of illuminated objects; furthermore, the illumination device generates diffuse light with high CCT, which simulates the light of the sky and gives the shadows a blue tone.

The patent application PCT/IB2013/060141, filed on 14 Nov. 2013, describes an illumination device based on the fact that, given a light source which stands out against a background and is observed by an observer through a Rayleigh diffuser panel, the observer has difficulty in perceiving the actual distance of the light source, if i) said distance is greater than a limit value, ii) the source is sufficiently intense to make focusing difficult by the observer and iii) the background is uniform (and, preferably, black). In practice, the illumination device is based on the fact that the observer is induced to perceive the light emitted by the diffuser panel as coming from a virtually infinite distance, provided that the light generated by the light source is within the observer's field of vision. In fact, the diffuser panel acts as a secondary light radiation source which, due to the high spatial uniformity, prevents the observer from evaluating the actual distance that separates him/her from the diffuser panel.

The illumination system described in the patent application PCT/IB2013/060141 allows very credible simulation of natural illumination conditions, and in particular allows the generation of visible optical stimuli comparable to those generated when a room is illuminated by a window. However, this illumination device is limited to artificially replicating stimuli of a mainly visible nature whereas, in reality, when an observer is in a room illuminated by a window, stimuli of different types can contribute to the overall perception of the observer.

DISCLOSURE OF INVENTION

The object of the present invention is therefore to provide an illumination device that solves at least partly the drawbacks of the known art.

According to the invention, an illumination device is provided as defined in the attached claims.

BRIEF DESCRIPTION OF THE DRAWINGS

For a better understanding of the invention embodiments are now described, purely by way of non-limiting examples, and with reference to the accompanying drawings, in which:

FIGS. 1, 4, 5, 9 and 10 show schematically cross sections of embodiments of the present illumination device, when coupled with a room;

BEST MODE FOR CARRYING OUT THE INVENTION

Figure 1:
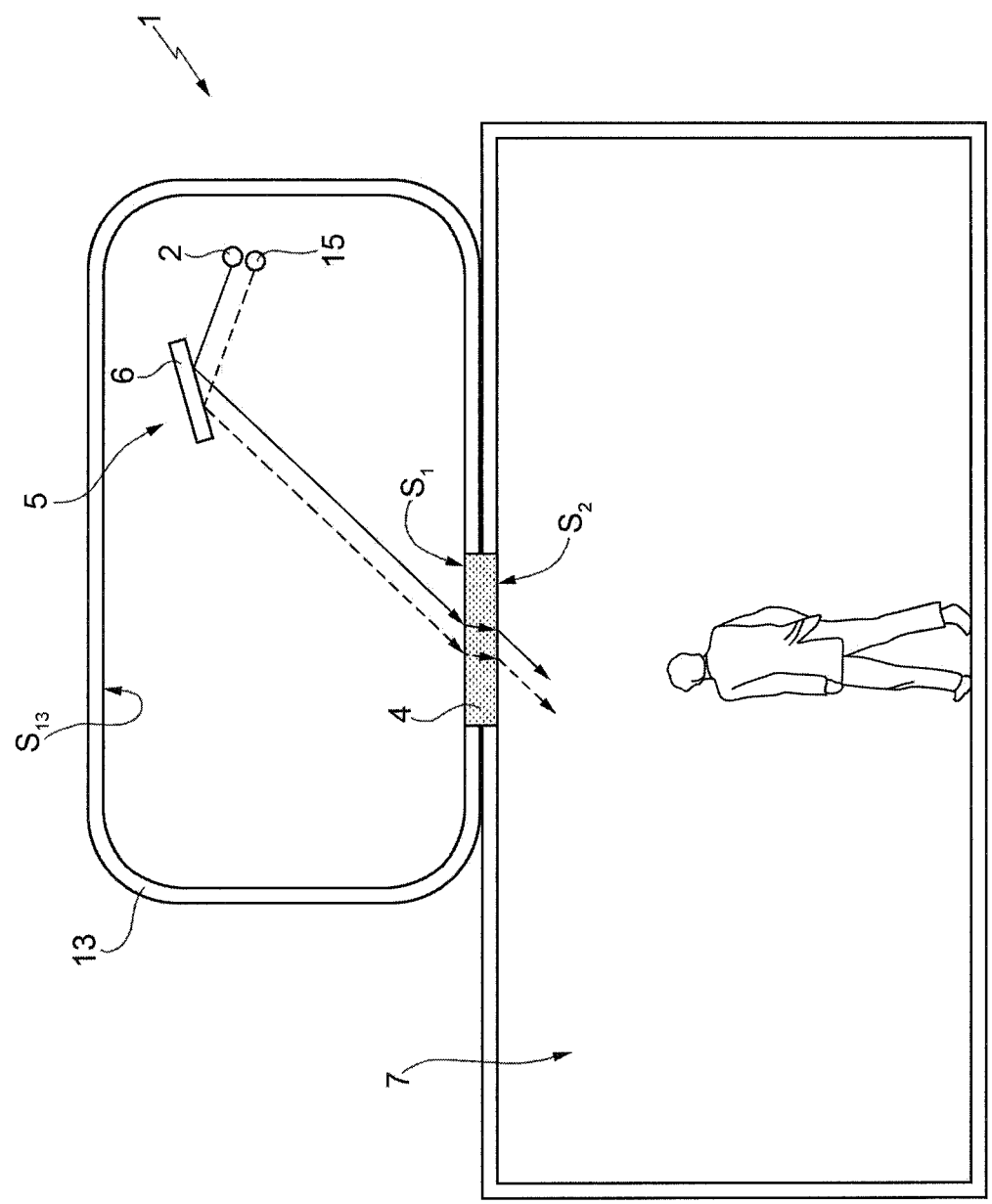

FIG. 1 shows an illumination device 1, which comprises a first optical source 2 and a first diffuser panel 4 which, without loss of generality, has the form of a parallelepiped and has a thickness, for example, ranging from 1 μm to 50 mm, preferably from 10 μm to 15 mm. Note that in the context of the present description, the term panel does not rule out the panel being flexible, instead of rigid.

The first diffuser panel 4 is delimited at the top and bottom by a first and a second surface $S_1$, $S_2$ respectively, parallel to each other. Furthermore, the illumination device 1 comprises a reflecting system 5, which includes at least one mirror 6 and is optically interposed between the first optical source 2 and the first diffuser panel 4.

The first optical source 2, which is referred to below as the first visible source 2, is preferably directional, i.e. apt to emit radiation in a solid emission angle below $4\pi$ sterad, for example below $2\pi$ sterad, preferably below $\pi$ sterad, even more preferably below $0.5*\pi$ sterad. Furthermore, the first visible source 2 emits mainly visible radiation, i.e. radiation with wavelength in the range between 400 nm and 700 nm; in particular, the first visible source 2 emits electromagnetic radiation having the majority of the radiant flux, for example at least 55%, preferably at least 70%, more preferably at least 80%, in the range between 400 nm and 700 nm. Below in the present description, this definition of visible radiation (ranging from 400 nm to 700 nm) is maintained.

In particular, the first visible source 2 emits visible light with a spectrum width $\Delta\lambda$ preferably greater than 100 nm, more preferably greater than 170 nm. The spectrum width $\Delta\lambda$ can be defined as the standard deviation of the wavelength spectrum of the first visible source 2.

Purely by way of example, the first visible source 2 may comprise a gas-discharge lamp, for example a plasma source, or may comprise:

an emitter (not shown) of optical radiation with short wavelength, i.e. in the region of the blue and/or the near ultraviolet (for example, a radiation in the range 350 nm-490 nm), this emitter operating for example on the basis of physical processes of spontaneous and/or stimulated emission and being formed, for example, of a LED or a laser; and an all-optical wavelength converter (not shown), which is apt to convert a first electromagnetic radiation, having wavelength within a first wavelength interval and formed for example of at least one part of the radiation emitted by the above-mentioned emitter, into a second electromagnetic radiation, having wavelength within a second wavelength interval, this second interval being formed at least partly by wavelengths longer than the wavelengths of the first interval; for example, the second electromagnetic radiation may have a wavelength ranging from 410 nm to 750 nm; furthermore, the all-optical converter may be formed of a phosphor or a system of phosphors.

In general, preferably, the first visible source 2 is formed of a source such that the dependence of the radiant flux spectrum density (i.e. the radiant flux per unit of wavelength) on the wavelength itself shows at least one peak in the visible region. The first visible source 2 is therefore formed, preferably, of a source different from a Planckian radiator, which is also known as thermal radiator with blackbody spectrum and is characterised by a radiant flux spectrum density which has a peak in the near infrared. (for example, at a wavelength of approximately 1 µm). The first visible source 2 is therefore different, for example, from an incandescent or halogen source.

Below the visible portion of the light emitted by the first visible source 2 will be referred to as the visible optical beam; furthermore, without any loss of generality, it is assumed that the first visible source 2 includes a respective collimator, of per se known type, such that the visible optical beam is collimated, or in any case, as previously mentioned, has a divergence of less than $2\pi$ sterad, preferably less than n sterad, even more preferably less than $0.5*\pi$ sterad.

Preferably, the maximum luminance of the first visible source 2 is greater than $0.1*10^6$ cd/m$^2$, preferably $10^6$ cd/m$^2$, even more preferably $10*10^6$ cd/m$^2$. For these values, in fact, the first visible source 2 generates a glare such that said first visible source 2 is difficult to observe directly.

The first visible source 2 and the reflecting system 5 are further preferably such that the illuminance profile on the first surface $S_1$ caused by the visible optical beam varies between a minimum value ILLU$_{min}$ and a maximum value ILLU$_{max}$, in which ILLU$_{min}$>⅓*ILLU$_{max}$, so as to limit the illuminance variations on the first diffuser panel 4. This illuminance uniformity condition can be obtained by interposing a "homogenising" optical system (not shown), for example free-form optics, or a Compound Parabolic Concentrator (CPC) or a plurality of CPCs, or a fly-eye system, such as a tandem array system, or a combination of the above systems, between the first visible source 2 and the first surface $S_1$ and/or by appropriately spacing the first visible source 2 from the first surface $S_1$.

Again with reference to the first diffuser panel 4, it operates as a Rayleigh diffuser, i.e. substantially it does not absorb the visible radiation and more effectively diffuses the short wavelength components of the incident light than the long wavelength components. In particular, the first diffuser panel 4 diffuses the light rays at a wavelength $\lambda$=450 nm (blue) at least 1.2 times, preferably at least 1.4 times, more preferably at least 1.6 times more effectively than the light rays at a wavelength $\lambda$=650 nm (red), the diffusion efficiency being given by the ratio between the radiant power of the diffuse light and the radiant power of the incident light.

In detail, assuming that a standard optical beam, generated by a dot-like light source according to standard D65 CIE (International Lighting Commission) arranged at a considerable distance from the first diffuser panel 4 (a beam, therefore, consisting of light rays parallel to one another) impinges perpendicularly on the first surface $S_1$, the first diffuser panel 4 is such that it separates the standard optical beam into the following components:

a transmitted component, formed of light rays of the standard optical beam which pass through the first diffuser panel 4 and are not subject to significant deviations, i.e. light rays that are subject to a deviation of less than 0.1°, with a light flux which is a fraction $\tau_{direct}$ of the overall light flux associated with the standard optical beam and impinging on the first diffuser panel 4;

a forward diffuse component, formed of light rays of the standard optical beam which come off the second surface $S_2$ in directions which are distributed around a direction perpendicular to the second surface $S_2$ (with the exception of this perpendicular direction and the directions which differ from this perpendicular direction by an angle of less than) 0.1°, with a light flux which is a fraction $\tau_{diffuse}$ of the overall light flux associated with the standard optical beam and impinging on the first diffuser panel 4;

a backward diffuse component, formed of light rays of the standard optical beam which come off the first surface $S_1$ in directions which are distributed around a direction perpendicular to the first surface $S_1$ (with the exception of this perpendicular direction and directions which differ from this perpendicular direction by an angle of less than 0.1°), with a light flux which is a fraction $\rho_{diffuse}$ of the overall light flux associated with the standard optical beam and impinging on the first diffuser panel 4; and a reflected component, formed of the light rays of the standard optical beam which come off the first surface $S_1$ in directions distributed around a direction perpendicular to the first surface $S_1$ and different from this perpendicular direction by an angle of less than 0.1°, with a light flux which is a fraction $\rho_{direct}$ of the overall light flux associated with the standard optical beam and impinging on the first diffuser panel 4.

In greater detail, the optical properties of the first diffuser panel 4 are such that:

$\tau_{diffuse}$ falls within the interval 0.05-0.5, preferably 0.07-0.4, more preferably 0.1-0.3, even more preferably 0.15-0.25;

the mean correlated colour temperature CCT_$\tau_{diffuse}$ of the forward diffuse component is significantly higher than the mean correlated colour temperature CCT_$\tau_{direct}$ of the transmitted component, i.e. CCT_$\tau_{diffuse}$>h*CCT_$\tau_{direct}$ with h=1.2, preferably h=1.3, more preferably h=1.5;

the first diffuser panel 4 does not significantly absorb the incident light, i.e. the sum $\tau_{direct}+\tau_{diffuse}+\rho_{direct}+\rho_{diffuse}$ is at least equal to 0.8, preferably 0.9, more preferably 0.95, even more preferably 0.97;

the first diffuser panel 4 diffuses mostly forward, i.e. $\tau_{diffuse} > \eta * \rho_{diffuse}$, in which $\eta$ is at least equal to 1.1, preferably $\eta=1.3$, more preferably $\eta=1.5$, even more preferably $\eta=2$; and the first diffuser panel 4 has a low reflection, i.e. $\rho_{direct}<0.09$ preferably $<0.06$, more preferably $<0.03$, even more preferably $<0.02$.

In structural terms, the first diffuser panel 4 comprises a solid matrix of a first material (preferably glass, or silica sol-gel, because it does not absorb visible and infrared radiation, or a thermoplastic resin, a thermosetting resin, a light-curing resin, an acrylic resin, an epoxy resin, a polyester-based resin, a polystyrene-based resin, a polyolefin resin, a polyimide resin, a polyimide resin, a polyvinyl alcohol-based resin, a butyral resin, a fluorine-based resin, a resin made of vinyl acetate or plastics such as polycarbonate, liquid crystal polymers, polyphenylene ether, polysulfone, polyethersulfone, polyarylate, amorphous polyolefin or mixtures or copolymers thereof), in which nanoparticles of a second material are dispersed (for example, an inorganic oxide such as $ZnO$, $TiO_2$, $ZrO_2$, $SiO_2$, $Al_2O_3$, or a polymer material, or a combination of two or more of these materials), the second material having a refractive index different from the refractive index of the first material. Both the first and the second material do not substantially absorb visible electromagnetic radiation. The first diffuser panel 4 is therefore without, for example, phosphors or fluorescent elements, although other embodiments are possible, not shown, in which the first diffuser panel 4 contains one or more of these elements.

Without any loss of generality, in the embodiment illustrated in FIG. 1 the first diffuser panel 4 is uniform in the sense that, given any point of the first diffuser panel 4, the physical characteristics of the first diffuser panel 4 at this point do not depend on the point itself. Furthermore, the first diffuser panel 4 is monolithic, i.e. the solid matrix does not have any discontinuity due to coupling by gluing or mechanical coupling. These characteristics of the first diffuser panel 4 are not necessary for the purposes of the present invention, but make the first diffuser panel 4 easier to manufacture.

In detail, the nanoparticles may be monodispersed; furthermore, the nanoparticles may have a spherical or other shape. The effective diameter. D of the nanoparticles (for a definition in the case of a non-spherical shape, see below) falls within the interval [5 nm-350 nm], preferably [10 nm-250 nm], more preferably [40 nm-180 nm], even more preferably [60 nm-150 nm], the effective diameter D being given by the product of the diameter of the nanoparticles by the refractive index of the first material.

The nanoparticles are further distributed inside the first diffuser panel 4 so that their area density, i.e. the number N of nanoparticles per square meter, i.e. the number of nanoparticles contained in a volume element having a parallelepipedal form, delimited at the top by a portion of the first surface $S_1$ having an area of 1 $m^2$, delimited at the bottom by a corresponding portion of the second surface $S_2$ having an area of 1 $m^2$, and having thickness equal to the thickness of the first diffuser panel 4, meets the condition $N \geq N_{min}$, in which:

$$N_{min} = \upsilon \frac{10^{-29}}{D^6} \cdot \left| \frac{m^2+2}{m^2-1} \right|^2$$

in which $\upsilon$ is a dimensional constant equal to $1*meters^6$, $N_{min}$ is expressed as number/$meter^2$, the effective diameter D is expressed in meters and m is equal to the ratio between the refractive index of the second material and the refractive index of the first material.

Without any loss of generality, below it is assumed that, inside the first diffuser panel 4, the nanoparticles are uniformly distributed, at least as regards the area density, i.e. it is assumed that the area density of the first diffuser panel 4 is substantially uniform; furthermore, in the present description, the area density is understood as defined on areas at least equal to $0.25=^2$.

Embodiments are nevertheless possible, not described further, in which the area density varies, so as to compensate for the illumination differences on the first diffuser panel 4, when illuminated by the first visible source 2. For example, the area density N(x,y) in a point (x,y) inside the first surface $S_1$ may be correlated with the illuminance ILLU(x,y) produced by the first visible source 2 in point (x,y), via the equation $N(x,y)=N_{mean}*I_{mean}/I(x,y)\pm5\%$, in which $N_{mean}$ and $I_{mean}$ are the mean illuminance and the mean area density, referring to the first surface $S_1$. In this case, the luminance of the first diffuser panel 4 is equalised, despite the non-uniformity of the illuminance profile of the first visible source 2 on the first diffuser panel 4. In this regard, it should be remembered that the luminance is the light flux in a beam that originates from a surface (or which falls on a surface) in a given direction, per unit of surface projected area, as seen in said direction, and per unit of solid angle, as contained for example in the ASTM (American Society for Testing and Materials) standard E284-09a.

Embodiments, not illustrated, are also possible which comprise one or more anti-reflection layers, arranged for example above the first surface $S_1$ and/or below the second surface $S_2$, for example in order to minimise $\rho_{direct}$.

It is also possible, as previously mentioned, for the nanoparticles not to have a spherical form; in this case, the effective diameter D can be defined as the effective diameter of the equivalent spherical particles, i.e. the effective diameter of the spherical particles having the same volume as the above-mentioned particles; in this regard, the equivalent spherical particles have a diameter known as equivalent diameter and such that the equivalent spherical particles have the same volume as the corresponding particles. Again, it is possible for the nanoparticles to be polydispersed, i.e. for the effective diameters of the nanoparticles to be distributed according to a distribution N(D). This distribution describes the number of nanoparticles per surface unit and per unit interval of effective diameter in the vicinity of the effective diameter D (i.e. the number of particles per surface unit having an effective diameter between $D_1$ and $D_2$ is equal to $$N_{D_2-D_1} = \int_{D_1}^{D_2} N(D)dD).$$

These effective diameters may be for example within the interval [5 nm-350 nm], i.e. the distribution can be non-null in this interval. In this case, considering that the diffusion efficiency increases approximately, i.e. within the limit of small particles, with the sixth power of the diameter of the nanoparticles, the polydispersed distribution acts more or less like a monodispersed distribution with a representative diameter $D'_{\it eff}$ defined as:

$$D'_{\it eff} = \left\{ \frac{\int N(D)D^6 dD}{N} \right\}^{1/6}$$

in which $$N = \int N(D)dD$$

$D'_{\it eff}$ may be selected so as to fall within the interval [5 nm-350 nm], preferably [10 nm-250 nm], more preferably [40 nm-180 nm], even more preferably [60 nm-150 nm].

Again with reference to the first diffuser panel 4 shown in FIG. 1, it is at least partially transparent in the visible range, therefore it allows the transmission of light apt to form images. In this regard, as previously mentioned, in the context of the present description, the light "transmitted" by an optical element is understood, unless specified otherwise, as the part of the light rays that impinge on the optical element and cross the optical element without undergoing a significant angular deviation, for example being deviated by an angle of less than 0.1°. Furthermore, an optical element is considered at least partially transparent for a given light beam impinging on it if it transmits at least a part of this light beam.

In particular, considering again the above-mentioned standard optical beam generated by a standard dot-like illumination source D65 arranged at a considerable distance from the first diffuser panel 4 and directed perpendicularly to the latter, the first diffuser panel 4 is such that at least 50%, preferably 70%, even more preferably 85% of the light rays of the standard optical beam are emitted by the first diffuser panel 4 within a cone with an angular aperture, measured as full width at half maximum (FWHM), no greater than 8°, preferably 4°, even more preferably 2°.

Again with reference to the embodiment shown in FIG. 1, without any loss of generality, the first visible source 2 is vertically misaligned with respect to the first diffuser panel 4, i.e. it is not intercepted by any axis perpendicular to the first and second surface $S_1$, $S_2$ and passing through these surfaces. Furthermore, the illumination device 1 is optically coupled with an environment, formed for example of a room 7 (i.e. a closed or in any case covered environment), via the first diffuser panel 4. In particular, the first diffuser panel 4 allows the first visible source 2 to be coupled to the room 7.

The illumination device 1 further comprises a background structure 13, shown only qualitatively in FIG. 1, which is also optically coupled to the room 7 via the first diffuser panel 4. In other words, optical rays which have struck the background structure 13 can enter the room 7 via the first diffuser panel 4, preferably exclusively.

In detail, the background structure 13 is delimited by a background surface $S_{13}$. Without any loss of generality, in the embodiment shown in FIG. 1, the background surface $S_{13}$ is without sharp edges and is closed, apart from an opening in the area of the first diffuser panel 4. Furthermore, again without any loss of generality, the background structure 13 is formed of a material which is optically absorbent in the visible range, for example a substantially black material with an absorption coefficient in the visible range greater than 70%, preferably greater than 90%, even more preferably greater than 97%. The background structure $S_{13}$ can therefore not be clearly seen by an observer located in the room 7, since it is poorly illuminated by the first visible source 2 and furthermore absorbs any radiation that strikes it, for example after this radiation has been reflected by the first diffuser panel 4.

In relation to the mirror 6, although in FIG. 1 it is schematically shown as a flat mirror, it may be of different type (for example, parabolic). Furthermore, although not shown, the reflecting system 5 may include further mirrors in addition to the mirror 6. For the sake of simplicity of description, below it is assumed that, even if further mirrors are present, the mirror 6 is the last mirror before the first diffuser panel 4; in other words, given an optical path which is formed of the reflecting system 5 and connects the first visible source 2 to the first diffuser panel 4, ed in particular to the first surface $S_1$, the mirror 6 causes a last deviation (i.e. a last direction variation) of the optical path, before the first diffuser panel 4.

In addition, the first diffuser panel 4 and the reflecting system 5 are arranged preferably so that no light ray coming from the first surface $S_1$ can be reflected by the reflecting system 5 so as to then impinge directly (i.e. without undergoing first at least one further reflection, for example by the background structure 13) on the first surface $S_1$. Therefore, no light ray coming from the room 7 and intersecting the first surface $S_1$ can impinge on the reflecting system 5 and be reflected by the latter directly on the first surface $S_1$.

In practice, the observer located inside the room 7 perceives the light rays coming from the second surface $S_2$ as if they were coming from a virtually infinite distance; furthermore, these light rays form a chromatic composition which simulates the natural illumination. In addition, the background structure $S_{13}$, like the reflecting system 5, is substantially invisible to the observer, since it provides a uniform background, preferably black, for the first visible source 2 and the infrared source 15.

The illumination device 1 also comprises a further optical source 15, which will be referred to below as the infrared source 15.

The infrared source 15 is preferably directional, i.e. apt to emit radiation in a solid emission angle less than $4\pi$ sterad, preferably less than $2\pi$ sterad, more preferably less than n sterad, even more preferably less than $0.5*\pi$ sterad. In this regard, the infrared source 15 may comprise for example an incandescent or halogen source, optically coupled with a respective collimator element (not shown), such as a parabolic cylinder, apt to limit the divergence of the radiation emitted by the incandescent or halogen source.

Furthermore, the infrared source 15 emits mainly infrared radiation, i.e. radiation with wavelength in the interval between 0.7 µm and 3 µm, which comprises the spectral region between 0.7 µm and 1.44 µm (also known as near infrared or IR-A) and the spectral region between 1.44 µm and 3 µm (also known as short wavelength infrared or IR-B).

In particular, the infrared source 15 emits electromagnetic radiation having the majority of the radiant flux, for example at least 55%, preferably at least 70%, more preferably at least 80%, in the interval between 0.7 µm and 3 µm.

The infrared source 15 may be such that the dependence of the radiant flux spectral density on the wavelength has a peak in the infrared, preferably in the region between 1 µm and 2.5 µm, more preferably between 1.2 µm and 2 µm, even more preferably between 1.3 µm and 1.6 µm. For said purpose, the infrared source 15 may be formed of a Planckian radiator, i.e. a blackbody spectrum thermal radiator, which preferably has a temperature in the interval 1160-2900K, more preferably 1450-2416K, even more preferably 1810-2230K. Furthermore, the infrared source 15 is preferably without all-optical wavelength converters, and in particular is without all-optical converters, for example phosphors.

For example, the infrared source 15 may be formed of a Planckian radiator at a temperature of 2070K, the radiant flux of which per unit of wavelength has a peak at 1.4 µm. Considering the form of the blackbody spectrum, and indicating by $P_{IR-A}$ and $P_{IR-B}$, respectively, the integral of the radiant flux per unit of wavelength between 0.7 µm and 1.44 µm and the integral of the radiant flux per unit of wavelength between 1.44 µm and 3 µm, we have $P_{IR-A}/P_{IR-B}=0.533$.

Below we refer to the portion in the infrared region of the light emitted by the infrared source 15 as the infrared optical beam. Furthermore, it is assumed below, as previously mentioned, that the infrared source 15 includes a respective collimator, of per se known type, so that the infrared optical beam is collimated, or in any case has a divergence of less than 2π sterad, preferably less than n sterad, more preferably less than 0.5*π sterad.

The infrared optical beam is conveyed by the reflecting system onto the first surface $S_1$ of the first diffuser panel 4. Furthermore, the arrangement of the first visible source 2 and of the infrared source 15 is such that the visible optical beam and the infrared optical beam impinge on the first surface $S_1$ overlapping at least partly. Preferably, the visible optical beam and the infrared optical beam overlap in an area at least equal to 50%, preferably 60%, even more preferably 70% of the largest of the two areas intercepted on the first surface $S_1$ by the visible optical beam and the infrared optical beam respectively.

In view of the above, substantially the infrared optical beam crosses the first diffuser panel 4, analogously to what occurs with the transmitted, component of the visible optical beam, therefore it is subject to a very limited diffusion, preferably null, by the first diffuser panel 4. For example, the diffuse component of the infrared optical beam has a radiant flux of less than 15%, preferably less than 10%, more preferably less than 5% of the radiant flux of the infrared optical beam. Therefore, the transmitted part of the visible optical beam (which below is again referred to as the visible optical beam) and the transmitted part of the infrared optical beam (which below is again referred to as the infrared optical beam) are again overlapped on at least part of the second surface $S_2$ and propagate in directions very near to each other.

In detail, on the second surface $S_2$, the infrared optical beam and the visible optical beam are again overlapped on an area at least equal to 50%, preferably 60%, even more preferably 70% of the largest of the two areas intercepted on the second surface $S_2$ by the visible optical beam and the infrared optical beam respectively. Furthermore, the infrared optical beam and the visible optical beam remain overlapped in a volume of space arranged downstream of the second surface $S_2$ and delimited partly by the latter. In addition, preferably, at least one portion of this volume is delimited partly by the second surface $S_2$ and is such that, in each point of said portion of volume, the direction of maximum radiance of the visible optical beam is near the direction of maximum radiance of the infrared optical beam, i.e. these two directions coincide, or in any case do not differ from each other by more than 40°, preferably 30°, even more preferably 20°. In this regard, by radiance of a beam in a given plane we mean the radiant flux per unit of surface and solid angle emitted in a given point and in a given direction.

In addition, for each point of the above-mentioned portion of volume, as also on the first and second surface $S_1$, $S_2$, the width of the angular radiance peak of the visible optical beam is less than 15°, preferably less than 10°, even more preferably less than 5°, while the width of the angular radiance peak of the infrared optical beam is less than 30°, preferably less than 20°, even more preferably less than 10°. Lastly, for some configurations, this portion of volume may extend preferably for at least one meter, more preferably at least two meters, even more preferably at least three meters downstream of the surface $S_2$, in an arbitrary direction.

The above-mentioned characteristics allow the observer to perceive the light and the heat as coming substantially from the same direction. Furthermore, the limited widths of the angular radiance peaks allow the visible optical beam and the infrared optical beam to generate shadows of objects illuminated by them; again, if the observer passes from shadow to light, he/she perceives the visible radiation and the thermal heat in a substantially simultaneous manner.

In practice, assuming for example that the observer's face is illuminated both by radiation generated by the first visible source 2 and by radiation generated by the infrared source 15, he/she will perceive his/her face as being heated from the same direction from which the visible light comes, analogously to what occurs in nature.

Figure 2:
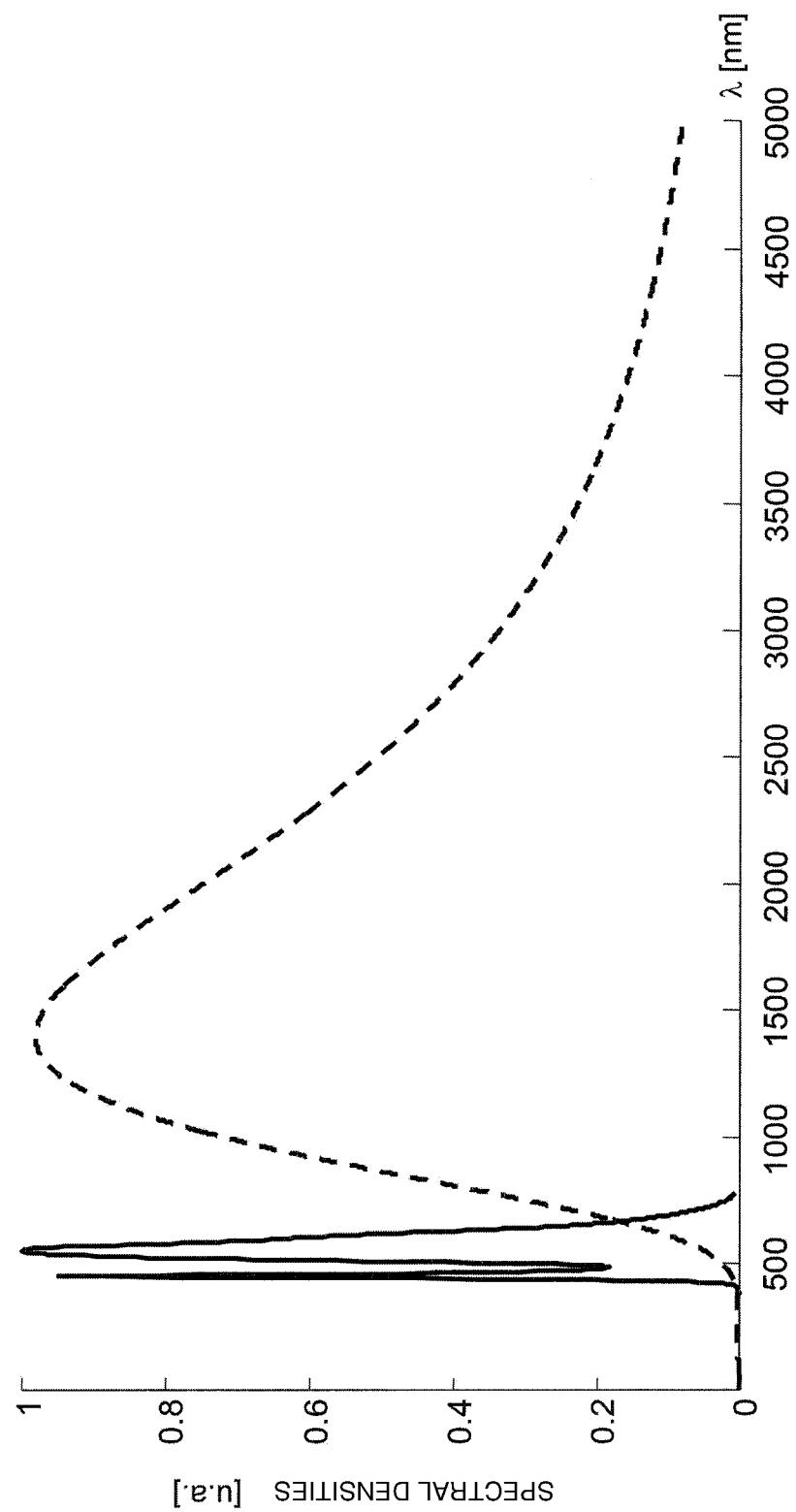
FIG. 2 shows the profile according to the wavelength of the radiant fluxes of two optical sources which form the present illumination device.

Furthermore, the first visible source 2 and the infrared source 15 are different from each other and generate the respective beams independently, on the basis of different physical phenomena (for example, spontaneous/stimulated emission associated with optical conversion if necessary, or blackbody emission). Therefore, considering overall the visible optical beam and the infrared optical beam, the radiant flux per unit of wavelength associated with them may exhibit at least one peak in the visible region (for example, at 470 nm) and one peak in the infrared region (for example, at 1.4 µm), as shown for example in FIG. 2. In detail, FIG. 2 shows in a qualitative manner examples of spectral density of radiant fluxes, as a function of the wavelength, relative to the first visible source 2 and to the infrared source 15.

Furthermore, indicating by $P_{vis}$ the integral in the visible region of the spectrum of the radiant flux per unit of wavelength emitted by the first visible source 2, and indicating by $P_{IR}$ the integral in the infrared region of the spectrum of the radiant flux per unit of wavelength emitted by the infrared source 15, we have preferably $P_{vis}/P_{IR}<0.3$, more preferably $P_{vis}/P_{IR}<0.1$, even more preferably $P_{vis}/F_{IR}<0.05$.

In addition, indicating by $P_{IR-A}$ the integral between 0.7 µm and 1.44 µm of the radiant flux per unit of wavelength emitted by the infrared source 15, and indicating by $P_{IR-B}$ the integral between 1.44 µm and 3 µm of the radiant flux per unit of wavelength emitted by the infrared source 15, we have preferably $P_{IR-A}/P_{IR-B}<2$, more preferably $P_{IR-A}/P_{IR-B}<1$, even more preferably $P_{IR-A}/P_{IR-B}<0.7$.

In view of the above, the luminance values of the first visible source 2, as said between $0.1*10^6$ cd/m² and $10*10^6$ cd/m², and the values of the above-mentioned ratios $P_{vis}/P_{IR}$ and $P_{IR-A}/P_{IR-B}$ differ from the corresponding values which occur in nature. In fact, the sun has a luminance of approximately $1.6*10^9$ cd/m² and a spectral radiant flux density similar to a Planckian curve with maximum corresponding to the temperature of approximately 5776 K. Therefore, the ratio $P_{vis-SUN}/P_{IR-SUN}$ between the integrals of the spectral radiant flux density in the visible region and in the infrared region is equal to approximately 0.76. Furthermore, the ratio $P_{IR-A-SUN}/P_{IR-B-SUN}$ between the integrals of the spectral radiant flux density in the near infrared and in the short wavelength infrared is equal to approximately 3.93.

The Applicants have noted, however, that the values proposed, associated with the possibility of independently controlling the spectral radiant flux density of the first visible source 2 and of the infrared source 15, allow effective simulation of the radiative effect induced on the observer by the solar radiation, simultaneously optimising the energy saving. In fact, in the first place, the perception of a natural visible illumination can be obtained also by adopting a visible source having luminance decidedly lower than that of the sun (for example, also one hundred or one thousand times lower), on condition that the spatial and spectral characteristics of the radiation, and in particular of the different contributions provided by the sky and the sun, are accurately reproduced. This occurs because the eye is provided with a diaphragm (the pupil), which is able to regulate the radiation flux which strikes the retina, obtaining similar perception levels in contexts with a great variety of illuminance. However, as regards detection of the infrared radiation by the observer's skin, this regulation capacity is absent. Therefore, a much weaker infrared radiation (for example one hundred or one thousand times weaker) than the solar radiation is not perceived as natural. For these reasons, the fact of having $(P_{vis}/P_{IR}) < (P_{vis\text{-}SUN}/P_{IR\text{-}SUN})$ contributes to improving the naturalness of the perception induced in the observer.

As regards again the perception of the heat induced by the infrared optical beam, it depends on the quantity of radiation absorbed by the skin, due to absorption by the water. Since this absorption increases as the wavelength increases, starting from approximately 1.4 µm, the relation $(P_{IR\text{-}A}/P_{IR\text{-}B}) < (P_{IR\text{-}A\text{-}SUN}/P_{IR\text{-}B\text{-}SUN})$ does not affect the naturalness of the perception and allows reduction of the energy consumption; in fact, for the purposes of induction of the perception of the heat, the radiation in the region IR-A is less effective than the radiation in the region IR-B.

On the basis of the above, it is evident that the visual and thermal effects of solar radiation, as perceived by an observer, are effectively reproduced by the present illumination device.

Figure 3:
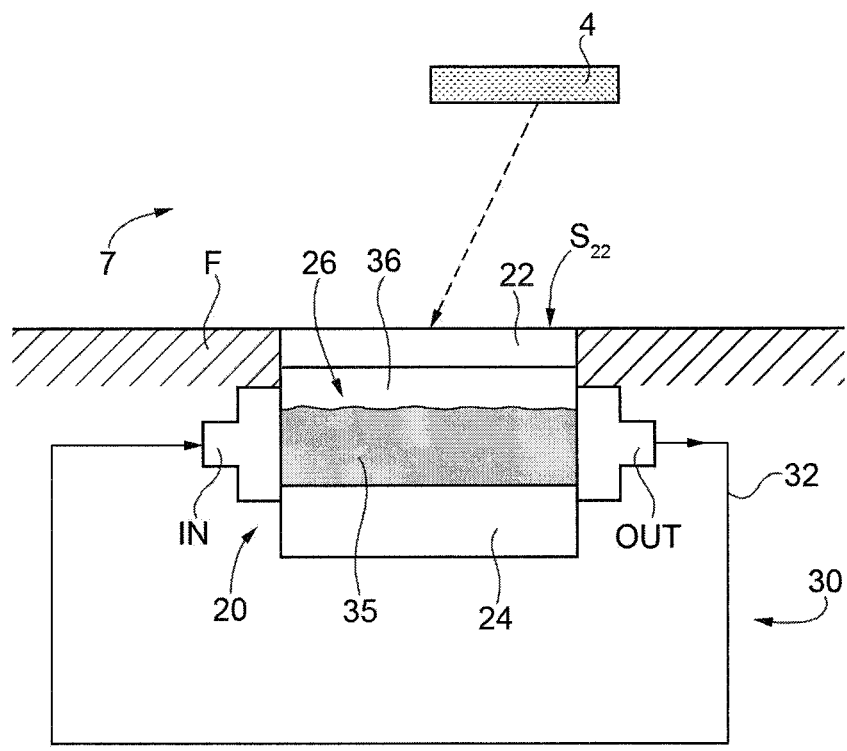
FIGS. 3 and 8 show schematically cross sections of portions of embodiments of the present illumination device.

FIG. 3 shows a further embodiment, in which the illumination device 1 comprises a heating module 20, integrated for example in the floor of the room 7, indicated by F.

In detail, the heating module 20 comprises an upper region 22, apt to be walked over by the observer and having a stratified form. The upper region 22 is formed for example of glass, or in any case of a material having substantially null absorption, or in any case very weak, in the infrared and in the visible regions.

The heating module 20 further comprises a lower region 24, formed for example of white sand or light-coloured pebbles, or in any case of a material which substantially does not absorb the visible radiation that strikes it, but diffuses it back (therefore, reflects it) so as to act as a secondary source of diffuse light. The lower region 24 is arranged below the upper region. 22 and at a distance from the latter, so that the upper region 22 and the lower region. 24 delimit a cavity 26.

The cavity 26 forms part of a fluidic circuit 30. In particular, the fluidic circuit 30 comprises, in addition to the cavity 26, a duct 32 (shown only schematically in FIG. 3); furthermore, the cavity 26 is in fluidic communication with the fluidic circuit 30 through an inlet port IN and an outlet port OUT.

Inside the fluidic circuit 30 a fluid 35 circulates (for example a liquid, like water); furthermore, the cavity 26 receives the incoming fluid 35 via the inlet port IN, while it supplies the outgoing fluid 35 through the outlet port OUT. The fluid 35 therefore crosses the cavity 26. Furthermore, preferably, the fluid 35 does not completely fill the cavity 26, but occupies only a lower portion of it; in this case, as shown in FIG. 3, an upper portion of the cavity 26 (indicated by 36) is occupied by air 4.

The heating module 20 is arranged in such a way that the infrared optical beam illuminates at least a part of a summital surface $S_{22}$, which delimits at the top the upper region 22. Furthermore, the fluid 35 (for example, liquid) does not substantially absorb in the visible region, therefore it does not absorb the visible optical beam, but absorbs in the infrared region, and therefore absorbs the infrared optical beam; for example, for the absorption coefficient $\alpha_{1.4\mu m}$, of the fluid 35 at the wavelength $\lambda=1.4$ µm preferably the relation $\alpha_{1.4\mu m} \geq 0.1$ cm$^{-1}$ applies, more preferably $\alpha_{1.4\mu m} \geq 0.3$ cm$^{-1}$, even more preferably $\alpha_{1.4\mu m} \geq 1$ cm$^{-1}$. Furthermore, defining $\alpha_{vis\text{-}MAX}$ as the maximum value of the absorption coefficient of the fluid 35 in the visible region, preferably the relation $\alpha_{vis\text{-}MAX}/\alpha_{1.4\mu m} < 0.4$ applies, more preferably $\alpha_{vis\text{-}MAX}/\alpha_{1.4\mu m} < 0.3$, even more preferably $\alpha_{vis\text{-}MAX}/\alpha_{1.4\mu m} < 0.2$.

In use, the infrared optical beam heats the fluid 35, which subsequently conveys the heat absorbed, for example to different portions of the room 7, or to the outside of the room 7, according to the form of the duct 32. In a per se known manner, the duct 32 may for example form heating coils (not shown); furthermore, the fluidic circuit 30 may include, for example, one or more hydraulic pumps (not shown) and/or one or more valves (not shown), for example electronically controllable.

Preferably, also the visible optical beam coming off the second surface $S_2$ is conveyed to at least one part of the summital surface $S_{22}$. Subsequently, the visible optical beam crosses the upper region 22 and the fluid 35, until it impinges on the lower region 24, where it is diffused, again in the direction of the room 7, thus contributing to illumination of the latter.

In practice, the embodiment shown in FIG. 3 allows improvement of the comfort produced in the room 7 and optimisation of the heat distribution. In particular, this embodiment allows recovery of part of the heat associated with the infrared optical beam to heat non-illuminated portions of the room 7 or of the outside world, i.e. portions of space where an individual, not being directly heated by the infrared optical beam, needs to benefit from a higher air temperature than the portions of space crossed by the infrared optical beam.

Figure 4:
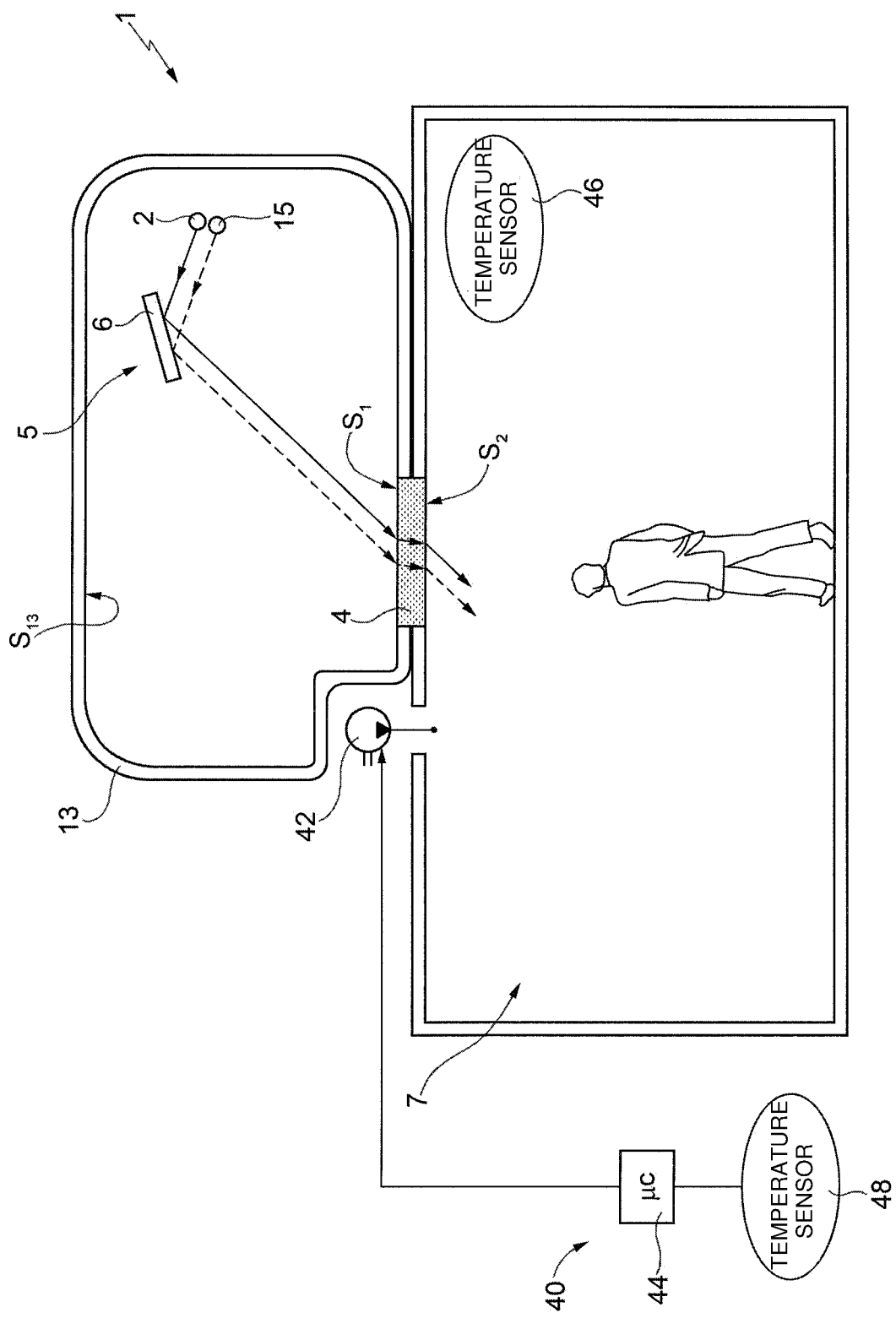

According to a different embodiment, shown in FIG. 4, the illumination device 2 includes a ventilation system 40. Without any loss of generality, it is assumed that in the embodiment shown in FIG. 4 the heating module 20 is absent, although embodiments are nevertheless possible comprising both the ventilation system 40 and the heating module 20.

In detail, the ventilation system 40 comprises a fluidic pump 42 of the electronically controllable type. The suction side of the fluidic pump 42 communicates, for example, with an environment outside the room 7; the discharge side of the fluidic pump 42 is in fluidic communication with the room 7, for example via an inlet opening. The room 7 further comprises an air discharge opening, not shown, positioned for example far from the discharge side of the fluidic pump 42.

The ventilation system 40 further comprises a control unit 44 and a first and a second temperature sensor 46, 48. The first temperature sensor 46 is arranged inside the room 7 and supplies a first electric signal, indicative of the temperature of a corresponding portion of the room 7, which will be referred to below as the first temperature; the second temperature sensor 48 is arranged outside the room 7 and supplies a second electric signal, indicative of the temperature of a corresponding portion of a space outside the room 7, which will be referred to below as the second temperature.

In detail, the control unit 44 is electrically connected to the fluidic pump 42, so as to control the fluidic pump 42. Furthermore, the control unit 44 is electrically connected to the first and to the second temperature sensor 46, 48, so as to receive the first and the second electric signal (for the sake of simplicity, the connection to the first temperature sensor 46 is not shown in FIG. 4).

In further detail, the control unit 44 operates the fluidic pump 42 so that the latter generates an air flow, for example of pulsed type. Generation of the air flow may be conditional upon verification, by the control unit 44, of a difference between the first and the second temperature at least equal to a threshold value.

Again in further detail, according to one embodiment, the ventilation system 40 produces the movement of large volumes of air in a very short time. For example, the ventilation system 40 may operate alternating periods of ON with periods of OFF so that, in one hour, the total duration $\tau_{ON}$ of the ON periods and the total duration $\tau_{OFF}$ of the OFF periods are preferably such that $\tau_{ON}/\tau_{OFF} \leq 0.3$, more preferably $\tau_{ON}/\tau_{OFF} \leq 0.1$, even more preferably $\tau_{ON}/\tau_{OFF} \leq 0.03$. According to a further variation, the ventilation system 40 may operate periodically and with a duty cycle no higher than 0.3, preferably no higher than 0.01, even more preferably no higher than 0.03. Furthermore, regardless of the ON and OFF timing, the fluidic pump 42 may comprise a bellows, or in any case can be connected to a storage chamber.

According to a further embodiment, the ventilation system 40 is such that, indicating by V the volume of the room 7 and by I the volume of air introduced in one second into the room 7, we have $I/V \leq 5*10^{-3}$ $s^{-1}$, preferably $I/V \geq 10^{-2}$ $s^{-1}$, even more preferably $I/V \geq 5*10^{-2}$ $s^{-1}$; furthermore, each pulse has a duration of at least one second, preferably three seconds, even more preferably five seconds.

Again, regardless of the above-mentioned details, the opening for introduction of the air into the room 7 preferably has a section with area for example equal to $\varepsilon * V^{2/3}$, with E in the interval [0.03-1], preferably [0.08-0.4], even more preferably [0.15-0.3]; in this case, the discharge opening of the room 7 may have a section with area no less than 50% of the area of the intake opening section.

In general, inside the room 7 a movement is created, preferably pulsed, of air masses having different temperature from that of the room 7, analogously to what would occur if, in place of the first diffuser panel 4, there were a window open onto the outside world. For this purpose, it is preferable for the intake opening to be near the first diffuser panel 4; for example, it is preferable for the intake opening to be at a distance from the first diffuser panel 4 of less than five meters, preferably three meters.

Figure 5:
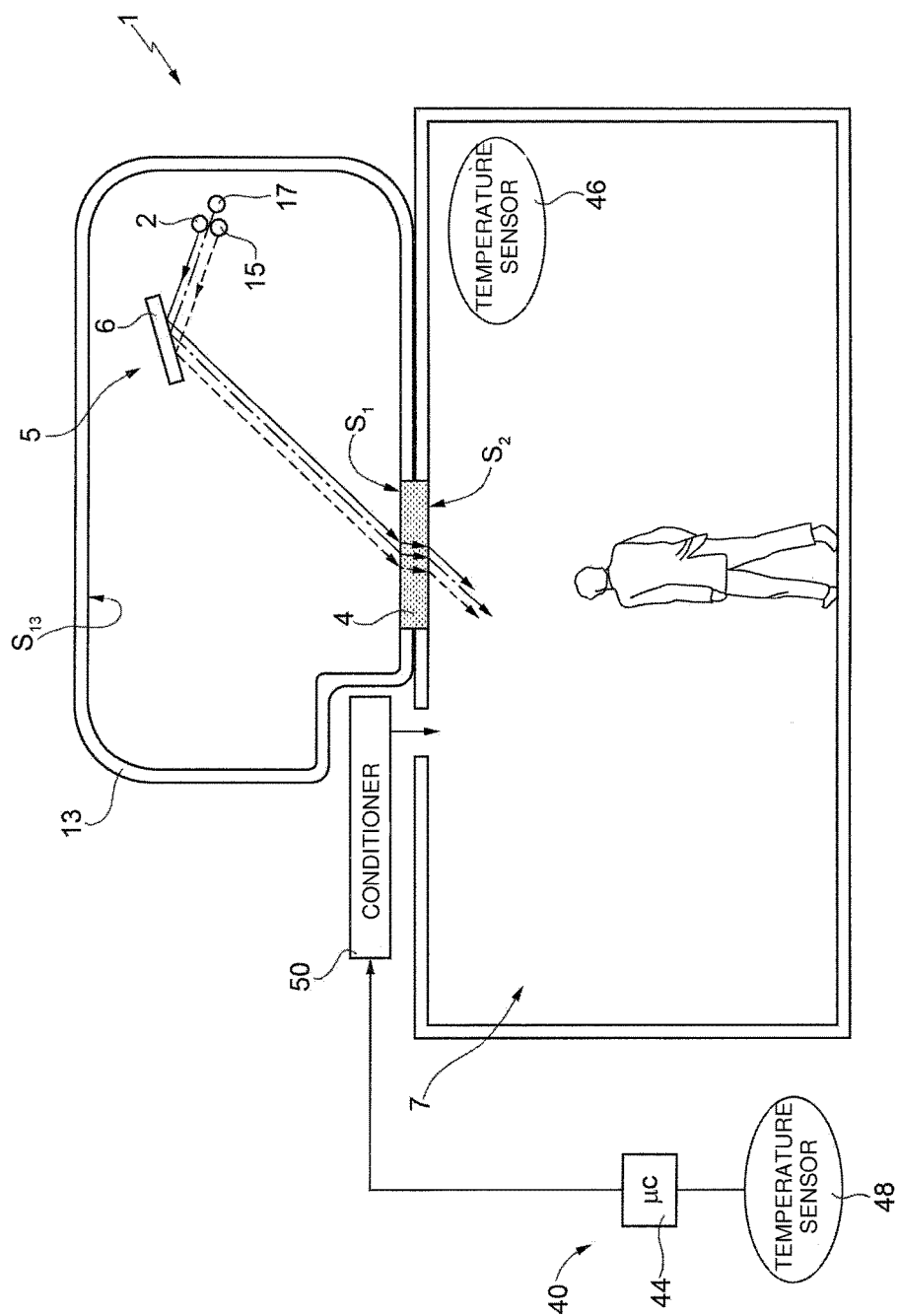

As shown in FIG. 5, the illumination device 1 may also comprise a conditioning unit 50, which includes the fluidic pump 42 (not shown in FIG. 5) and is controlled by the control unit 44, so that the air taken into the room 7 substantially has a third temperature. In this way, the illumination device 1 also implements a climate control system of the room 7. In the winter, this system can operate alternatively to the heating system, injecting in pulsed mode volumes of air at a higher temperature than the temperature of the room 7.

In further detail, the ventilation system 40 is configured to introduce, preferably in pulsed mode, masses of air into the room 7, at a different temperature from that of the room 7, even if the outside of the room 7 is at the same temperature as the room 7. In particular, if the first and second temperature differ by more than one predefined thermal differential, the conditioning unit 50 does not condition the temperature of the air taken in, which is therefore equal to the second temperature; if, on the other hand, the first and the second temperature differ by less than the predefined thermal differential, the conditioning unit 50 is not limited to taking air into the room 7 from the outside, but thermally conditions it, so as to impose a minimum temperature difference with respect to the temperature of the room, and operating in heating or in cooling mode, according to the desired temperature value in the room 7.

The embodiment shown in FIG. 5 also comprises a further optical source 17, which emits an optical beam in the near ultraviolet region, and in particular in the interval 300 nm-400 nm; for example, this optical beam may have 97% of the radiant flux in the WA region (315 nm-400 nm) and the remaining 3% in the UVB region. This optical source and the beam emitted by it will be referred to below as ultraviolet source 17 and ultraviolet optical beam respectively. The ultraviolet source 17 is different from the first visible source 2 and from the infrared source 15 and generates the ultraviolet optical beam by means of a physical phenomenon preferably different from the emission phenomena that characterise the first visible source 2 and the infrared source 15.

In general, the ultraviolet source 17 may be added to each of the embodiments described in the present description. For practical purposes, the ultraviolet source 17 allows the observer, when illuminated by the ultraviolet optical beam, to get a tan.

Preferably, the ultraviolet source 17 includes a collimator; furthermore, preferably, the ultraviolet optical beam impinges on the first surface $S_1$ overlapping at least partly the visible optical beam and the ultraviolet optical beam. In addition, at least part of the ultraviolet optical beam is transmitted from the first diffuser panel 4; therefore, coming off the second surface $S_2$, the transmitted part of the ultraviolet optical beam is still at least partly overlapping both the visible optical beam and the infrared optical beam. However, embodiments are possible in which the ultraviolet source 17 is arranged, for example, inside the room 7. For example, the ultraviolet source 17 may be arranged in the vicinity of the first diffuser panel 4.

Figure 6:
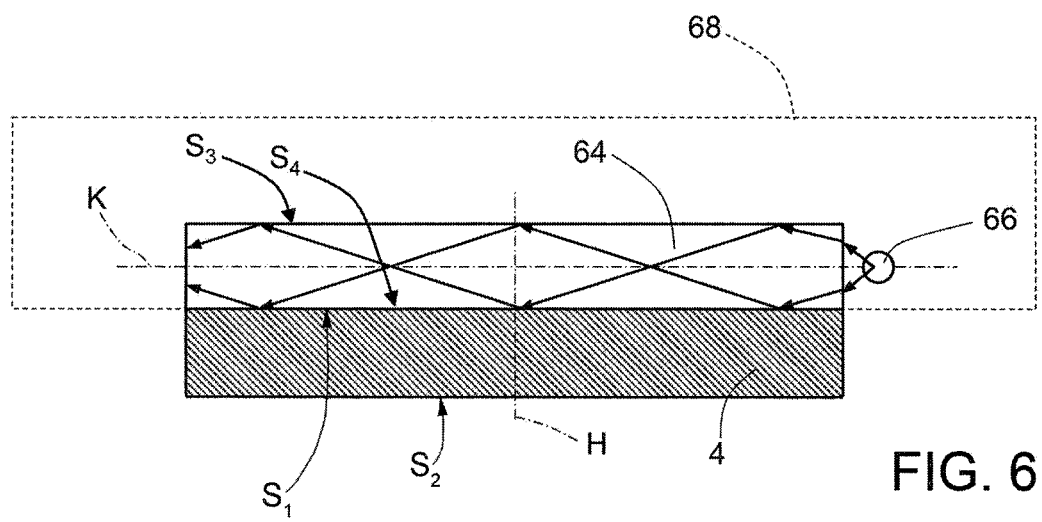
FIGS. 6 and 7a-7b show qualitatively cross sections of corresponding portions of embodiments of the present illumination device.

As shown in FIG. 6, the lighting system 1 may include a second diffuser panel 64 and a second visible source 66, which form an auxiliary generator of diffuse visible light 68, additional to the first diffuser panel 4, and which will be referred to below as auxiliary generator 68. Furthermore, the auxiliary generator 68 is described below with reference to FIG. 6 which does not show, among other things, either the first visible source 2, or the infrared source 15, or the reflecting system 5; in any case, the auxiliary generator 68 may be incorporated in each of the embodiments described in the present description.

In detail, the second diffuser panel 64 has for example the shape of a parallelepiped and is arranged above the first diffuser panel 4, with which it is in direct contact. The second diffuser panel 64 is therefore delimited at the top and bottom by a third and a fourth surface $S_3$, $S_4$ respectively, the fourth surface $S_4$ being in contact with the first surface $S_1$. Furthermore, indicating by K the optical axis of the waveguide formed by the second diffuser 64, the second diffuser panel 64 has a thickness, measured in a direction perpendicular to the third and fourth surface $S_3$, $S_4$, and therefore perpendicular to the axis K, less than the length, measured along the axis K.

The second diffuser panel 64 is substantially transparent to radiation which propagates, for example, along an axis H perpendicular to the first, to the second, to the third and to the fourth surface $S_1$, $S_2$, $S_3$, $S_4$ and passing through the geometric centres of these four surfaces; in other words, the second diffuser panel 64 does not diffuse this radiation. Therefore, the second diffuser panel 64 is substantially transparent to the visible optical beam and the infrared optical beam, i.e. it does not diffuse these two beams. Furthermore, the second diffuser panel 64 acts as a diffuser for the radiation which propagates along the axis K.

The second visible source 66 is arranged laterally to the second diffuser panel 64, so that the visible radiation emitted by the second visible source 66, which is referred to below as the auxiliary optical beam, is optically guided along the second diffuser panel 64.

The second diffuser panel 64 may be formed, for example, of a commercial diffuser apt to be illuminated laterally, for example "Acrylite® LED" or "Plexiglas® LED End-Lighten". In particular, the second diffuser panel 64 is formed of a third material (for example, a material selected from the materials previously listed with reference to the first material), in which microparticles of a fourth material are dispersed (for example ZnO, $TiO_2$, $ZrO_2$, $SiO_2$, $Al_2O_3$); the third and the fourth material do not substantially absorb visible radiation or infrared radiation. Furthermore, the diameters (equivalent if necessary) of the microparticles may vary from 2 µm to 20 µm.

In use, part of the radiation guided by the second diffuser panel 64 comes out of the second diffuser panel 64, after being propagated in a guided manner along a part of the second diffuser panel 64, due to the diffusion performed by the microparticles contained in the second diffuser panel 64 (the diffusion is not shown in FIG. 6).

The auxiliary generator 68 allows variation of the colour and the intensity of the diffuse visible light generated by the illumination device 1, substantially without varying the colour and the intensity of the visible light transmitted.

Although not shown, at least one of the third or fourth surfaces $S_3$, $S_4$ of the second diffuser panel 64 may also be surface-machined so as to make it rough. This roughness contributes to the diffusion by the second diffuser panel 64 on the auxiliary optical beam. In this case, the second diffuser panel 64 may be without microparticles. Regardless of the presence of the roughness and/or the microparticles, the first and the second diffuser panel 4, 64 may be positioned at a distance from each other and/or the second diffuser panel 64 may be positioned below the first diffuser panel 4.

The auxiliary generator 68 may also be formed, rather than, of the second diffuser panel 64 and the second visible source 66, of an OLED layer (not shown), known per se, which is able to generate diffuse visible light having colour and intensity which can be varied in an electronically controllable manner. Furthermore, the OLED layer is substantially transparent vis-á-vis the visible optical beam and the infrared optical beam.

Embodiments are also possible (not shown) in which the first diffuser panel 4 is absent, but the auxiliary generator 68 is present. In this case, the auxiliary generator 68 generates the entire diffuse visible light produced by the illumination device 1.

In practice, the present illumination device makes the experience of the observer in the room 7 more similar to the situation in which the room 7 is illuminated by a window onto the real world, open if necessary. Therefore, the embodiments described previously involve optically coupling the infrared source 15 and the first visible source 2 with a diffuse light generator, which comprises the first diffuser panel 4 and/or the auxiliary generator 68. The diffuse light generator includes an optical structure delimited by an inner surface, facing towards the first visible source 2, and an outer surface, facing towards the room 7. The inner surface is formed, according to the embodiment considered, of the first or third surface $S_1$, $S_3$, while the outer surface is formed, according to the embodiment considered, of the second or fourth surface $S_2$, $S_4$. Furthermore, the optical structure is configured to receive the visible optical beam, generated by the first visible source 2, and i) to be at least partially transparent to the visible optical beam, therefore to transmit at least part of the visible optical beam, and ii) to emit diffuse visible light from the outer surface, which is formed of visible light which i subject, within the optical structure, to an angular deviation at least equal to 0.1°, induced in a substantially causal manner by the nanoparticles encountered. In practice, the part of visible optical beam transmitted by the optical structure forms direct visible, and therefore directional, light downstream of the optical structure, which has crossed the optical structure (in particular, the first diffuser panel 4 and/or the second diffuser panel 64) in a substantially deterministic manner, while the diffuse visible light is to a first approximation without directionality.

More specifically, the diffuse light generator is configured to generate, coming off the outer surface, transmitted visible light having a CCT lower than the CCT of the diffuse visible light. Furthermore, the diffuse light generator is such that the CCT of the diffuse visible light is higher than the CCT of the transmitted visible light; even more specifically, the CCT of the transmitted visible light is no higher than the CCT of the visible optical beam generated by the first visible source 2.

The advantages offered by the present illumination device emerge clearly from the preceding description. In particular, the present illumination device induces in the user a perception of heat, as if he/she were illuminated by the sunlight. Furthermore, the present illumination device allows effective use of the heat generated and, in some embodiments, emulation of the effect of air movement which occurs in the presence of an open window.

Lastly it is evident that modifications and variations can be made to the present illumination device, without departing from the scope of the present invention, as defined by the attached claims.

Figure 7A:
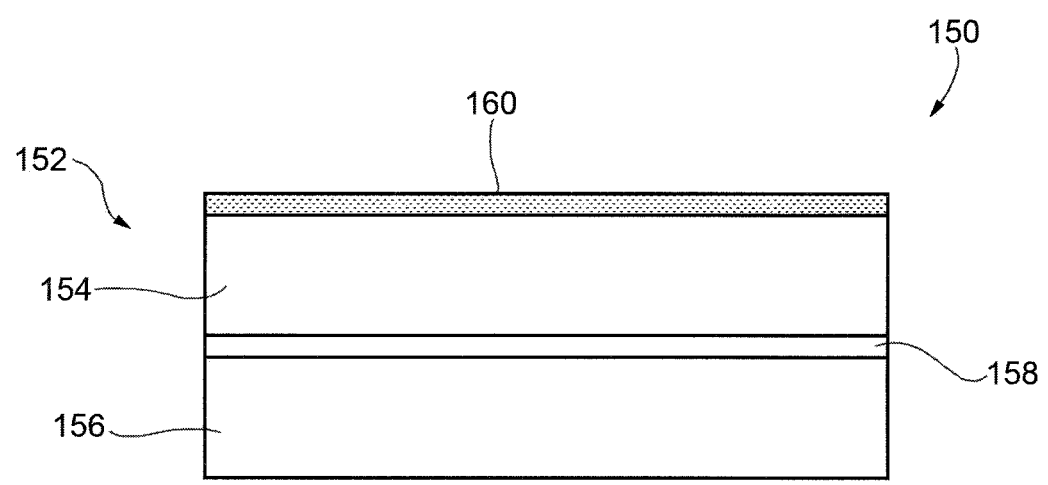

The first diffuser panel 4, as shown in FIG. 7a, may be replaced by a stratified structure 150, which includes a supporting structure 152 comprising at least one first supporting layer 154, formed for example of glass, preferably toughened, or in any case a material that does not absorb either in the visible or in the infrared region. Without any loss of generality, in the embodiment shown in FIG. 7a, the supporting structure 152 further comprises a second supporting layer 156, formed for example of glass, preferably toughened, or in any case a material that does not absorb either in the visible or in the infrared region; the second supporting layer 156 is arranged below the first supporting layer 154 and at a distance from the latter. Furthermore, the supporting structure 152 comprises a gluing layer 158, interposed between the first and the second supporting layer 154, 156, with which it is in direct contact; the gluing layer 158 fixes the first and the second supporting layer 154, 156 to each other and is formed for example of a film of a polymer adhesive material, such as ethylene vinyl acetate (EVA) or polyvinyl butyral (PVB), the characteristics and thickness of which are such as to make it substantially non-absorbent in both the infrared and the visible region. Above the first supporting layer 154, and in direct contact with the latter, a layer 160 extends, which is referred to as the diffuser layer 160. The diffuser layer 160 is formed for example of a film of polymer material (for example, an acrylic or polyamide or polyurethane or epoxy or alkyl resin, or a polyester-based resin, or a mixture of at least two of the preceding resins) which is non-absorbent both in the visible and in the infrared region, has for example a thickness of between 1 μm and 300 μm and, unlike the supporting structure 152, contains within it nanoparticles having the diameters described relative to the preceding embodiments. Furthermore, optically, the diffuser layer 160 has the same behaviour as the first diffuser panel 4, in terms of characteristics (for example, CCT) of the transmitted portion of the visible optical beam and of the diffuse visible light, and in terms of behaviour in frequency and behaviour in the case of illumination by means of the above-mentioned standard optical beam generated by a standard dot-like illumination source D65 arranged at a considerable distance.

Figure 7B:
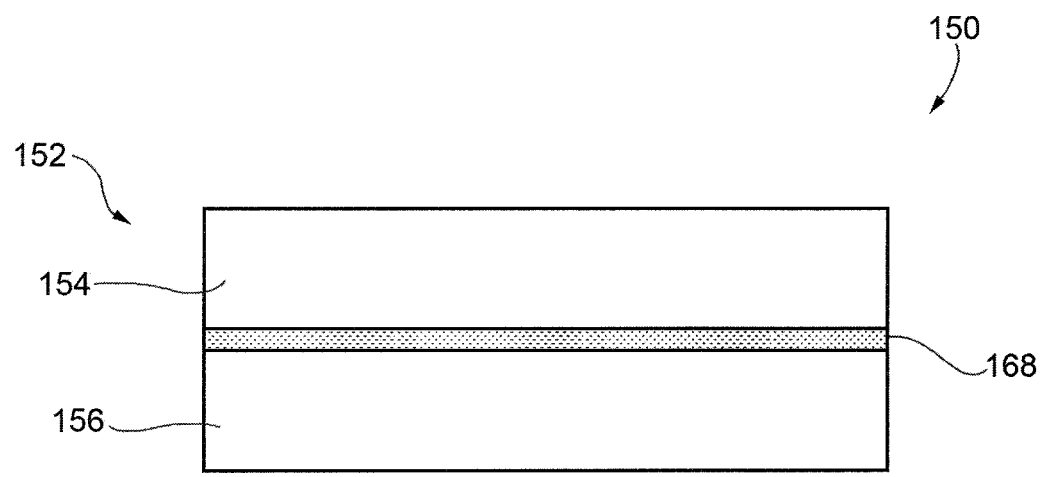

As shown in FIG. 7b, the nanoparticles may also be contained within the supporting structure 152, and in particular within the gluing layer, here indicated by 168, in which case the diffuser layer 160 may be absent, since this gluing layer 168 acts as a diffuser layer. In this case, the thickness of the gluing layer 168 may be, for example, between 1 μm and 300 μm.

Although not shown, the stratified structure 150 may further comprise a first and/or a second anti-reflection layer. The first anti-reflection layer may be arranged above the diffuser layer 160 (if present), or above the first supporting layer 154; the second anti-reflection layer may be arranged below the second supporting layer 156.

In general, as previously explained, both in the case of the presence of the first diffuser panel 4, and in the case of the presence of the diffuser layer, each of them is preferably formed of a matrix of material which does not absorb either in the visible or in the infrared region. Embodiments are possible, however, in which the matrix is formed of a material having a non-negligible absorption coefficient, for example in the infrared region. In this case, the thickness of the element (panel or layer) formed by the matrix may be reduced, so that the element (panel or layer) does not absorb, in the case of normal incidence, more than 20%, preferably more than 10%, even more preferably more than 5% of the radiant flux of the infrared optical beam.

The background structure 13 (when present) may be different from what is shown. In fact, it is sufficient for the background structure 13 to have geometric and/or light absorption characteristics such that, when the first and, if present, the second visible source 2, 66 are switched on, a first structure condition applies, described herebelow with reference to FIG. 8 and observed also by the embodiments previously described, for example the embodiment shown in FIG. 1.

Figure 8:
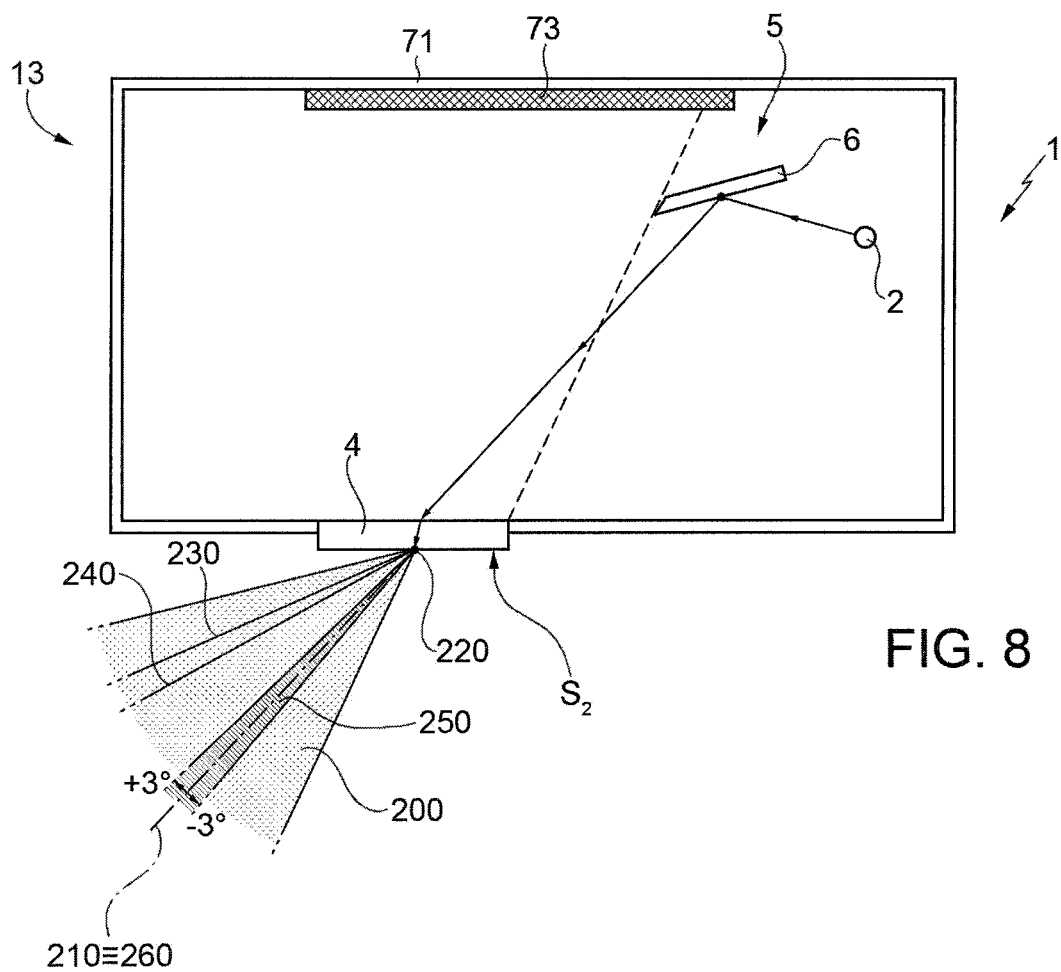

For the sake of simplicity, and without any loss of generality, in FIG. 8 the first visible source 2 is of the dot-like type; furthermore, in FIG. 8 the angles are shown in a qualitative manner. Again in the embodiment shown in FIG. 8, the background structure 13 is formed of a supporting structure 71, which is referred to below as the frame 71, and an absorbent element. 73, which internally coats a portion of the frame 71 and has a substantially uniform absorption coefficient in the visible region and/or has an absorption coefficient in the visible region at least equal to 70%, preferably 90%; furthermore, the absorbent element 310 is preferably without sharp edges and has an area at least equal to 50%, preferably 80%, of the first surface $S_1$.

Therefore, according to the above-mentioned first structure condition, given a direction beam (for example, conical) 200 with an angle at the vertex of at least 0.1 sterad and with a beam axis 210, in any first point 220 of at least one portion of the second surface $S_2$ having area equal to at least 50%, preferably 80%, even more preferably 100%, of the area of the entire second surface $S_2$, a first and a second luminance of the first point 220, referred to below as the first and second background luminance, differ from each other by no more than 50% of the first background luminance. In greater detail, the first and the second background luminance are measured respectively along a first and a second direction of observation 230, 240, the first direction of observation 230 belonging to the direction beam 200 and being different from each of the local glare directions 250, the second direction of observation 240 being at an angular distance of between 0.3° and 1° from the first direction of observation 230 and being different from each of the local glare directions 250, the local glare directions 250 being the directions that are less than 3° from any direction 260 under which any point of the first visible source is seen from the first point 220 (assuming a dot-like source, one single direction 260 is present in FIG. 8). In greater detail, each of the first and second background luminance is formed only of the light rays which have struck the background structure 13 and have never crossed the room 7 (the latter not being shown in FIG. 8), and therefore which have never crossed the second surface $S_2$ coming from the room 7.

For example, referring to any one of the first or second background luminance, it can be measured in the hypothesis of the first diffuser panel 4 being coupled to a first anechoic chamber in the visible region, i.e. assuming that the room 7 absorbs 100% of the incident light, and carrying out the steps of:
    after replacing the background structure 13 with a second anechoic chamber in the visible region, measuring the luminance L1 of the above-mentioned first point 220, in the first direction of observation 230; and subsequently
    removing the second anechoic chamber and providing the background structure 13; subsequently
    measuring the luminance L2 of the first point 220, again in the first direction of observation 230; and
    calculating the difference between the luminance L2 and the luminance L1.

As shown again in FIG. 8, the beam axis 210 may coincide with the direction 260 under which the first visible source 2 is seen from the first point 220. Furthermore, the direction beam 200 and the relative orientation with respect to the first diffuser panel 4 do not vary with respect to the position of the above-mentioned first point 220 on the second surface $S_2$.

As previously mentioned, the first structure condition can be observed by adopting different technical solutions, of per se known type. For example, in the case of the embodiment shown in FIG. 8, the form, composition and arrangement of the absorbent element 73 are such that the first structure condition is observed.

In each of the embodiments described, the background structure may furthermore be such as to meet a second structure condition, i.e. prevent, when the first visible source 2 is switched on, the above-mentioned first background luminance from being above a luminance limit value equal to 30% of the total luminance of the first point 220 in the first direction of observation 230, this total luminance being measured assuming the absence of light rays coming from the room 7, and therefore with the aid of the above-mentioned first anechoic chamber.

Embodiments as described previously, but in which the respective background structures 13 are such that the second structure condition is met, but the first structure condition is not met, are also possible.

With reference to the embodiments that include the heating module 20, it is also possible to interpose an optical element, for example a mirror arranged on a wall of the room, between the first diffuser panel 2 and the upper region 22. For example, FIG. 9 shows an embodiment comprising a reflecting surface 320, arranged on a wall of the room 7. Without any loss of generality, the embodiment shown in FIG. 9 is without the background structure 13 and the reflecting system 5, in addition to the ventilation system 40; furthermore, again without any loss of generality, the embodiment shown in FIG. 9 is without the auxiliary generator 68.

In detail, the reflecting surface 320 is arranged downstream of the first diffuser panel 4, is delimited by an edge 321 and is arranged so that at least one portion of it is illuminated, together with a corresponding edge portion 321, by the visible optical beam. This portion of the reflecting surface 320 has an area at least equal to 50%, preferably 70%, even more preferably 100%, of the area of the entire reflecting surface 320. Furthermore, this portion of the reflecting surface 320 is such that the shortest of the optical paths which connect the first visible source 2 to the reflecting surface 320 has a length equal to at least 50%, preferably 70%, even more preferably 100%, of the maximum distance between any two points of this illuminated portion of the reflecting surface 320. For practical purposes, the reflecting surface 320 acts as a visual reference and is apt to increase the depth of the field perceived by the observer; furthermore, the reflecting surface 320 is apt to reflect the infrared optical beam, transmitted from the first diffuser panel 4, towards the heating module 20.

As shown in FIG. 10, embodiments are also possible in which the visual reference is formed of a diaphragm. 350 between two environments, which delimits a corresponding opening 351, which establishes optical communication between the two environments. The opening 351 therefore forms an immaterial surface (apart from the edge), is delimited by a respective edge 352 and is arranged so that at least one portion of it is illuminated, together with a corresponding portion of the edge 352, by the visible optical beam. This portion of the opening 351 has an area at least equal to 50%, preferably 70%, even more preferably 100%, of the area of the entire opening 351. Furthermore, the illuminated portion of the opening 351 is such that the shortest of the optical paths that connect the first visible source 2 to the opening 351 has a length equal to at least 50%, preferably 70%, even more preferably 100%, of the maximum distance between any two points of the above-mentioned illuminated portion of the opening 351. In this case, furthermore, the heating module 20 is arranged preferably outside the room 7, so as to intercept the infrared optical beam, after the latter has crossed the opening 351.

Each of the above-mentioned illuminated portions of the reflecting surface 320 and of the opening 351 has an area at least equal to $1/10$, preferably $3/10$, even more preferably $1/2$, of the area of the second surface $S_2$.

The infrared source 15 may be arranged so that the infrared optical beam impinges on the first surface $S_1$ without having crossed the reflecting system 5. Moreover, as previously mentioned, in general the reflecting system 5 may be absent, and likewise the background structure 13. If the reflecting system 5 is absent, both the first visible source 2 and the infrared source 15 may be arranged above the first diffuser panel 4 and in line with the latter, i.e. in directions perpendicular to the first and the second surface $S_1$, $S_2$ and passing through the latter.

Figure 11:
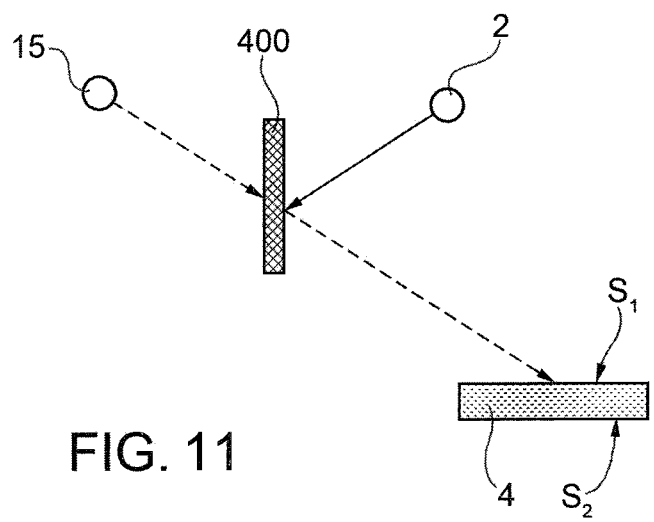
FIG. 11 shows a block diagram of a portion of an embodiment of the present illumination device.

FIG. 11 shows an embodiment comprising an optical beam splitter 400, which couples the visible optical beam, generated by the first visible source 2, and the infrared optical beam, generated by the infrared source 15. Without any loss of generality, the embodiment shown in FIG. 11 is without the reflecting system 5 and the auxiliary generator 68.

In detail, the optical beam splitter 400 is a dichroic element of per se known type and acts as an optocoupler. In particular, the optical beam splitter 400 is arranged so as to receive the infrared optical beam, generated by the infrared source 15, and transmit it in a first direction, such that the infrared optical beam then impinges on the first diffuser panel 4. Furthermore, the optical beam splitter 400 is arranged so as to receive the visible optical beam, generated by the first visible source 2, and reflect it in the first direction, so that it subsequently impinges on the first diffuser panel 4. Furthermore, embodiments are possible comprising, in addition to the optical beam splitter 400, the reflecting system 5, optically interposed between the first visible source 2 and the optical beam splitter 400. Furthermore, variations are possible in which the optical beam splitter reflects the infrared optical beam and transmits the visible optical beam.

The heating module 20 may be without the lower region 24. Again, the heating module 20 may be arranged, for example, on a wall of the room 7. Furthermore, the connections between the control unit 44 and the first and second temperature sensors 46, 48 and (if present) the conditioning unit 50 may be of the wireless type.

In addition, the first and, if present, the second diffuser panel 4, 64 may have different forms, not necessarily with constant thicknesses. Furthermore, the first and the second diffuser 4, 64 do not have to be parallel to each other.

Variations are possible, each formed of a corresponding embodiment from among the embodiments described previously, but without the infrared source 15. These variations may or may not comprise the ultraviolet source 17.

Embodiments of the type previously described are also possible, in which the first surface S1 is at least equal to ten times, more preferably three hundred times, even more preferably ten thousand times the area of the biggest out of: 1) the projection area of the emission surface (i.e. the surface that emits photons) of the first visible source 2 on a plane perpendicular to the direction of maximum radiance of the visible optical beam; and 2) the area of the projection of the emission surface of the infrared source 15 on a plane perpendicular to the direction of maximum radiance of the infrared optical beam.

Lastly, according to a further example (not shown), the present device for illuminating an environment includes: a first visible optical source configured to emit a visible optical beam; a diffuse light generator including an optical structure delimited by an inlet surface and an outlet surface, the inlet surface being configured to receive the visible optical beam, the diffuse light generator being configured to emit from the outlet surface diffuse visible light and direct visible light, the direct visible light being formed of a portion of visible optical beam which is transmitted from the optical structure. The illumination device further includes an infrared optical source, different from the first visible optical source and configured to emit an infrared optical beam so that it impinges on the inlet surface, the optical structure being configured to transmit at least a first portion of the infrared optical beam. Furthermore, the illumination device comprises a ventilation system which can be coupled to the environment and configured to introduce air masses into the environment.

The invention claimed is:

1. An illumination device for an environment, the illumination device configured to simulate an open window and comprising:
   a first visible optical source configured to emit a visible optical beam;
   a diffuse light generator including an optical structure delimited by an inlet surface and by an outlet surface, the inlet surface being configured to receive the visible optical beam, said diffuse light generator being configured to emit from the outlet surface diffuse visible light and direct visible light, said direct visible light being formed by a portion of visible optical beam which is transmitted by the optical structure;
   an infrared optical source, different from the first visible optical source and configured to emit an infrared optical beam so that it impinges on the inlet surface, said optical structure being configured to transmit at least one first portion of the infrared optical beam; and
   a ventilation system in fluid communication with the environment and configured to introduce air masses into the environment in pulsed mode.

2. The illumination device according to claim 1, wherein the ventilation system is configured to alternate periods of on and periods of off such that, in one hour, the total duration $\tau_{ON}$ of the on periods and the total duration $\tau_{OFF}$ of the off periods are such that $\tau_{ON}/\tau_{OFF} \leq 0.3$.

3. The illumination device according to claim 1, wherein the environment has a volume V; and wherein the ventilation system is configured to introduce into the environment a volume of air I per second; and wherein $I/V \geq 5*10^{-3} s^{-1}$.

4. The illumination device according to claim 3, wherein the ventilation system is configured to introduce said air masses into the environment through an intake opening having a section with area equal to $\varepsilon*V^{2/3}$, with in the interval [0.03-1].

5. The illumination device according to claim 1, wherein the ventilation system is configured to introduce air masses having a temperature different from that of the environment.

6. The illumination device according to claim 1, wherein the ventilation system comprises:
   a temperature sensor configured to detect the temperature of a portion of the environment; and
   a conditioner configured so as to introduce said air masses with a temperature differing from the temperature detected by the temperature sensor by at least one predefined thermal differential.

7. The illumination device according to claim 6, wherein the ventilation system is configured to withdraw said air masses from a portion of space outside the environment; and wherein, if the air masses withdrawn have a temperature which differs from the temperature detected by the temperature sensor by less than said thermal differential, the conditioner thermally conditions the air masses withdrawn and subsequently introduces the conditioned air masses into the environment.

8. An illumination device for illuminating an environment, the illumination device comprising:
   a first visible optical source configured to emit a visible optical beam;
   a diffuse light generator including an optical structure delimited by an inlet surface and an outlet surface, the inlet surface being configured to receive the visible optical beam, said diffuse light generator being configured to emit from the outlet surface diffuse visible light and direct visible light, said direct visible light being formed by a portion of visible optical beam which is transmitted by the optical structure;
   an infrared optical source, different from the first visible optical source and configured to emit an infrared optical beam so that it impinges on the inlet surface, said optical structure being configured to transmit at least one first portion of the infrared optical beam; and
   a heating module arranged so as to receive said first portion of the infrared optical beam;
   wherein said heating module comprises a cavity optically accessible to said first portion of the infrared optical beam and further accessible to a fluid configured to absorb at least part of the first portion of the infrared optical beam, said cavity being in fluid communication with a hydraulic circuit.

9. The illumination device according to claim 8, wherein the heating module further comprises:
   an upper region, which delimits the cavity; and
   a lower region arranged so that, in use, the fluid is arranged between said lower region and the upper region, said lower region being designed to backward diffuse in the visible spectrum.

10. An illumination device for illuminating an environment, the illumination device comprising:
    a first visible optical source configured to emit a visible optical beam;
    a diffuse light generator including an optical structure delimited by an inlet surface and by an outlet surface, the inlet surface being configured to receive the visible optical beam, said diffuse light generator being configured to emit from the outlet surface diffuse visible light and direct visible light, said direct visible light being formed of a portion of visible optical beam which is transmitted from the optical structure;
    an infrared optical source, different from the first visible optical source and configured to emit an infrared optical beam so that it impinges on the inlet surface, said optical structure being configured to transmit at least one first portion of the infrared optical beam; and
    an ultraviolet optical source configured to emit an ultraviolet optical beam, so that it impinges on the inlet surface and is subsequently emitted from the outlet surface.

11. The illumination device according to claim 1, wherein the first visible optical source, the infrared optical source and the optical structure are configured so that, in use, the direct visible light and the first portion of the infrared optical beam are at least partially overlapped, in a volume of space arranged downstream of the outlet surface.

12. The illumination device according to claim 11, wherein, for each point of at least one portion of said volume of space, the direction of maximum radiance of the direct visible light is no more than 30° from the direction of maximum radiance of the first portion of the infrared optical beam.

13. The illumination device according to claim 10, wherein, within said portion of said volume of space, the width of the angular radiance peak of the direct visible light is below 15°, and the width of the angular radiance peak of the first portion of the infrared optical beam is below 30°.

14. The illumination device according to claim 1, wherein the first visible optical source is different from a Planckian radiator.

15. The illumination device according to claim 14, wherein the infrared source has no wavelength converters of the all-optical type.

16. The illumination device according to claim 1, wherein the ratio between the integral in the visible spectrum of the radiant flux per unit of wavelength emitted by the first visible optical source and the integral in the infrared spectrum of the radiant flux per unit of wavelength emitted by the infrared source is below 0.1.

17. The illumination device according to claim 1, further comprising a dichroic element arranged upstream of the optical structure and configured to optically couple the visible optical beam and the infrared optical beam, so that they are at least partly overlapping on the inlet surface.

18. The illumination device according to claim 1, further comprising a reflecting optical system configured to convey the visible optical beam and the infrared optical beam onto the inlet surface.

19. The illumination device according to claim 1, wherein the optical structure comprises a first diffuser element configured substantially not to absorb light in the visible spectrum and to more effectively diffuse the short wavelength components than the long wavelength components of the visible optical beam.

20. The illumination device according to claim 19, wherein the first diffuser element comprises a matrix of a first material, wherein first particles of a second material are dispersed, said first and second material having, respectively, a first and a second refractive index, said first particles having equivalent diameters such that the product of said equivalent diameters multiplied by the first refractive index is within the interval 5 nm-350 nm.

21. The illumination device according to claim 1, wherein the diffuse light generator (2,68) comprises:
a second visible optical source configured to emit visible light; and
a second diffuser element, optically coupled with the second visible optical source so that, in use, at least part of the visible light emitted by the second visible optical source is diffused by the second diffuser element, after propagating in a guided manner inside at least part of the second diffuser element.

22. The illumination device according to claim 1, wherein the diffuse light generator is such that the correlated color temperature (CCT) of the direct visible light is lower than the CCT of the diffuse visible light.

23. The illumination device according to claim 1, wherein the diffuse light generator is such that the correlated color temperature (CCT) of the direct visible light is no greater than the CCT of the visible optical beam generated by the first visible source.

24. The illumination device according to claim 1, wherein the diffuse light generator is such that the correlated color temperature (CCT) of the diffuse visible light is greater than the CCT of the visible optical beam generated by the first visible source.

25. The illumination device according to claim 1, further comprising a background structure configured to be optically coupled to the environment via the diffuse light generator and to provide a substantially uniform and preferably dark background for the first visible optical source.

26. The illumination device according to claim 25, wherein the background structure is configured so that, when the first visible optical source is switched on, and given a direction beam with an angle at the vertex of at least 0.1 sterad, at any first point of at least one portion of the outlet surface, a first and a second background luminance of said first point differ from each other by no more than 50% of the first background luminance; said first and second background luminances being measured respectively along a first and a second direction of observation, the first direction of observation belonging to the direction beam and being different from each of the local glare directions, the second direction of observation being at an angular distance ranging from 0.3° to 1° from the first direction of observation and being different from each of the local glare directions; said local glare directions being the directions that are less than 3° from any direction under which the first visible optical source is seen from said first point, each of said first and second background luminance being formed solely by light rays which have impinged onto the background structure and have never crossed the environment.

* * * * *